(12) United States Patent
Lewis (10) Patent No.: US 7,951,128 B1
(45) Date of Patent: May 31, 2011

(54) PROTECTIVE UNDERGARMENT SYSTEM

(76) Inventor: Della Lewis, South Holland, IL (US)

( * ) Notice: Subject to any disclaimer, the term of this patent is extended or adjusted under 35 U.S.C. 154(b) by 416 days.

(21) Appl. No.: 12/214,167

(22) Filed: Jun. 17, 2008

(51) Int. Cl.
*A61F 13/15* (2006.01)

(52) U.S. Cl. .................. 604/385.14; 604/386; 604/387; 604/393; 604/394

(58) Field of Classification Search ............. 604/385.14, 604/386, 387, 393, 394, 396
See application file for complete search history.

(56) References Cited

U.S. PATENT DOCUMENTS

| | | | |
|---|---|---|---|
| 4,022,212 A | 5/1977 | Lovison | |
| 5,325,543 A | 7/1994 | Allen | |
| 5,356,401 A | 10/1994 | Levari | |
| 5,593,398 A | 1/1997 | Weimer | |
| 5,944,708 A | 8/1999 | Philpott | |
| 6,156,951 A * | 12/2000 | Gustafsson et al. | 604/369 |
| 6,193,702 B1 | 2/2001 | Spencer | |

FOREIGN PATENT DOCUMENTS

WO   WO 98/43574   10/1998

* cited by examiner

*Primary Examiner* — Jacqueline F. Stephens
(74) *Attorney, Agent, or Firm* — Jeffrey A. Proehl; Woods, Fuller, Shultz & Smith, PC

(57) ABSTRACT

A protective undergarment system for absorbing fluids released by the body of a user. The protective undergarment system includes an upper member being designed for being selectively positioned around an abdomen, a groin and a posterior of the user. The upper member comprises a lower aperture extending through the upper member whereby the lower aperture is designed for extending from a portion of the groin to a portion of the posterior and passes between the legs of the user. A lower member is selectively coupled to the upper member whereby the lower member is selectively positioned over the lower aperture of the upper member to selectively close the lower aperture of the upper member. The lower member is designed for absorbing the fluids released by the body whereby the lower member can be removed from the lower member when the lower member is soiled.

20 Claims, 6 Drawing Sheets

PROTECTIVE UNDERGARMENT SYSTEM

CROSS REFERENCE TO RELATED APPLICATION

This application is a substitute for application Ser. No. 10/622,947, filed Jul. 18, 2003.

BACKGROUND OF THE INVENTION

1. Field of the Invention

The present invention relates to protective menstrual garments and more particularly pertains to a new protective undergarment system for absorbing fluids released by the body of a user.

2. Description of the Prior Art

The use of protective menstrual garments is known in the prior art. U.S. Pat. No. 6,193,702 describes a device for being worn by a user to absorb bodily fluids released by the body of the user. Another type of protective menstrual garment is U.S. Pat. No. 6,193,702 having a panty comprising a body portion and a crotch portion that is selectively coupled to the body portion with the crotch portion being able to receive a sanitary napkin. U.S. Pat. No. 6,409,712 has a shield that is positioned between the underwear and the user and is for protecting the underwear from being stained and soiled.

While these devices fulfill their respective, particular objectives and requirements, the need remains for a system that has certain improved features the comfort of a regular pair of underwear and provide the protection for the user.

SUMMARY OF THE INVENTION

The present invention meets the needs presented above by providing an upper member that conforms to the body of the user and a lower member that is selectively coupled over a lower aperture of the upper member to absorb fluids secreted by the body of the user and can be removed from the upper member and disposed of when soiled.

Still yet another object of the present invention is to provide a new protective undergarment system that increases the self esteem of the user by providing a body member that conforms to body to reduce visibility of the upper member under the clothes being worn by the user.

To this end, the present invention generally comprises an upper member being designed for being selectively positioned around an abdomen, a groin and a posterior of the user. The upper member comprises a lower aperture extending through the upper member whereby the lower aperture is designed for extending from a portion of the groin to a portion of the posterior and passes between the legs of the user when the upper member is being worn by the user. A lower member is selectively coupled to the upper member whereby the lower member is selectively positioned over the lower aperture of the upper member to selectively close the lower aperture of the upper member. The lower member is designed for absorbing the fluids, such as menstrual fluid and urine, released by the body whereby the lower member can be removed from the lower member when the lower member is soiled.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF PREFERRED EMBODIMENTS

With reference now to the drawings, and in particular to FIGS. 1 through 7 thereof, a new protective undergarment system embodying the principles and concepts of the present invention and generally designated by the reference numeral 10 will be described.

As best illustrated in FIGS. 1 through 4, a first embodiment of the protective undergarment system 10 generally comprises an upper member 11 being designed for being selectively positioned around an abdomen, a groin and a posterior of the user. The upper member 11 comprises a lower aperture 12 extending through the upper member 11 whereby the lower aperture 12 is designed for extending from a portion of the groin to a portion of the posterior and passes between the legs of the user when the upper member 11 is being worn by the user.

A lower member 13 is selectively coupled to the upper member 11 whereby the lower member 13 is selectively positioned over the lower aperture 12 of the upper member 11 to selectively close the lower aperture 12 of the upper member 11. The lower member 13 is designed for absorbing the fluids, such as menstrual fluid and urine, released by the body whereby the lower member 13 can be removed from the lower member 13 when the lower member 13 is soiled.

The upper member 11 comprises a pair of leg apertures 14 extending through the upper member 11. Each of the leg apertures 14 is designed for permitting a leg of the user to be extended through the upper member 11 when the upper member 11 is being worn by the user. The upper member 11 comprises a waist aperture 15. The waist aperture 15 is designed for receiving the waste of the user when the upper member 11 is being worn by the user.

The upper member 11 comprises a flexible material. The flexible material is designed for conforming to the abdomen, groin and posterior of the user to provide a comfortable fit for the user.

The lower member 13 comprises an absorbent material. The absorbent material is designed for absorbing the fluids released by the body of the user. The absorbent material is designed for being discarded to allow the user to reuse the upper member 11 when the lower member 13 becomes soiled.

The lower member 13 comprises a first fastener member 16 is positioned adjacent a perimeter edge 17 of the lower member 13. The upper member 11 comprises a second fastener member 18 whereby the second fastener member 18 is positioned adjacent the lower aperture 12 of the upper member 11. The first fastener member 16 is complimentary to the second fastener member 18 whereby the first fastener member 16 is selectively coupled to the second fastener member 18 to secure the lower member 13 to the upper member 11.

The first fastener member 16 comprises a first portion of hook and loop fastener 19. The second fastener member 18 comprises a second portion of hook and loop fastener 20. The first portion of hook and loop fastener 19 is complimentary to the second portion of hook and loop fastener 20 whereby the first portion of hook and loop fastener 19 is selectively coupled to the second portion of hook and loop fastener 20 to selectively couple the lower member 13 to the upper member 11. Alternately, the first fastener member 16 and the second fastener member 18 may comprise a zipper closure, hooks, buttons or tape.

The lower member 13 comprises pair of end portions 21 and a medial portion 22. The lower member 13 tapers from the end portions 21 to the medial portion 22 whereby the lower member 13 is substantially hourglass shaped. The medial portion 22 is designed for being positioned between the legs of the user to inhibit the lower member 13 from bunching up between the legs of the user and is uncomfortable for the user.

Significantly, the upper member may be continuous and unbroken along and about the upper aperture of the upper member, and the upper member may be continuous and unbroken along and about each the leg aperture of the pair of leg apertures. These features, especially in combination, allow the upper member to remain securely in place when the lower member is removed from the upper member for replacement. Thus, the upper member may have an edge that defines the upper aperture, and the edge that defines the upper aperture of the upper member may be continuous and unbroken along and about the upper aperture. Similarly, the upper member may have an edge that defines each of the leg apertures, and the edges that define the respective leg apertures may each be continuous and unbroken along and about each the leg aperture of the pair of leg apertures.

In use, the user couples the lower member 13 to the upper member 11. The legs of the user are slipped through the leg apertures 14 of the upper member 11 and slides the upper member 11 up the legs until the waist of the is positioned in the waist aperture 15 of the upper member 11 to provide a comfortable fit for the user the upper portion conforms to the body. As the user progresses through the day the user my remove the lower member 13 when the lower member 13 has become soiled and replaced with a new lower member 13.

Figure 1:
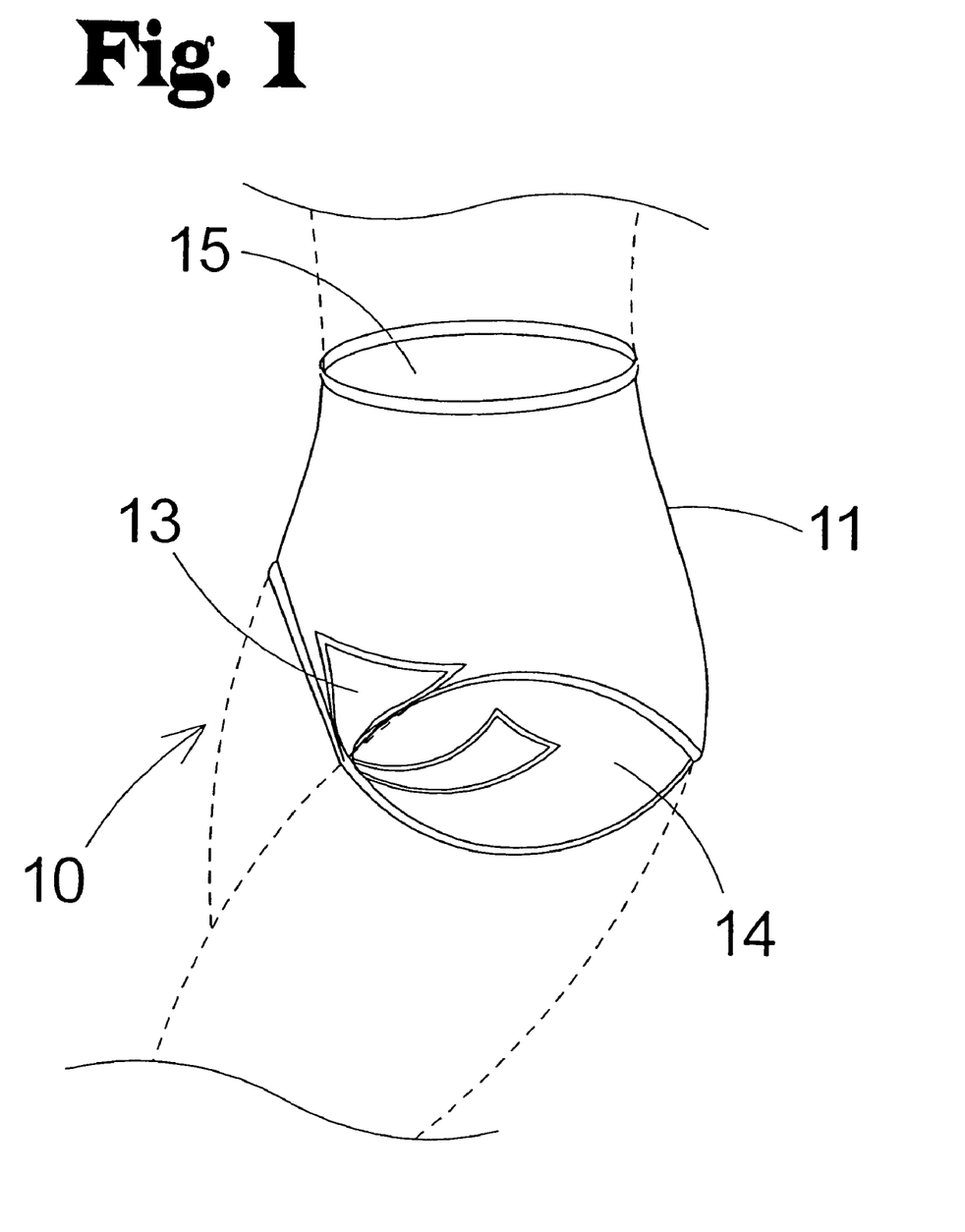
FIG. 1 is a perspective view of a new protective undergarment system according to the present invention for a female user.
Figure 2:
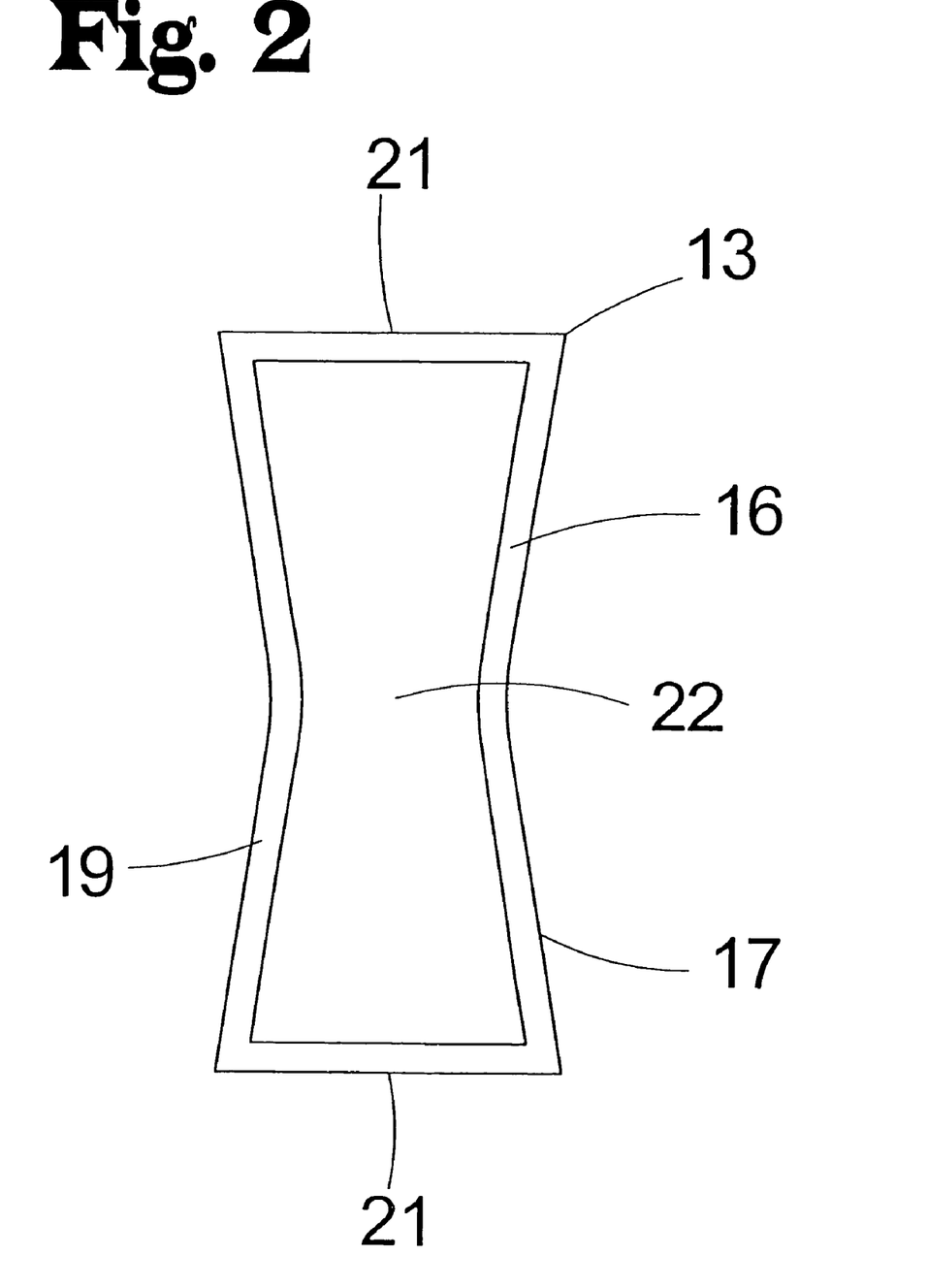
FIG. 2 is a top view of the lower member of the present invention.
Figure 3:
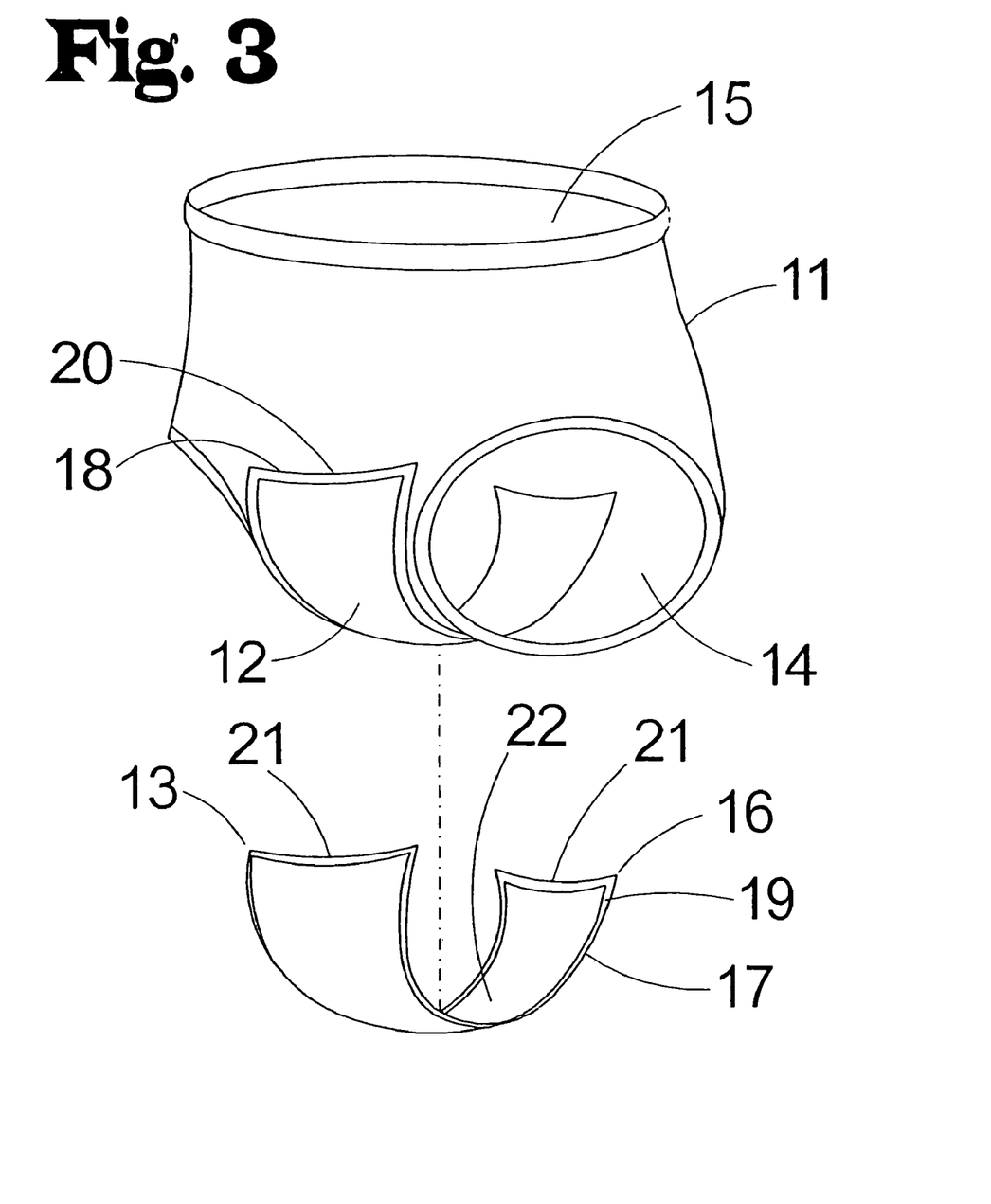
FIG. 3 is an exploded view of the present invention.
Figure 4:
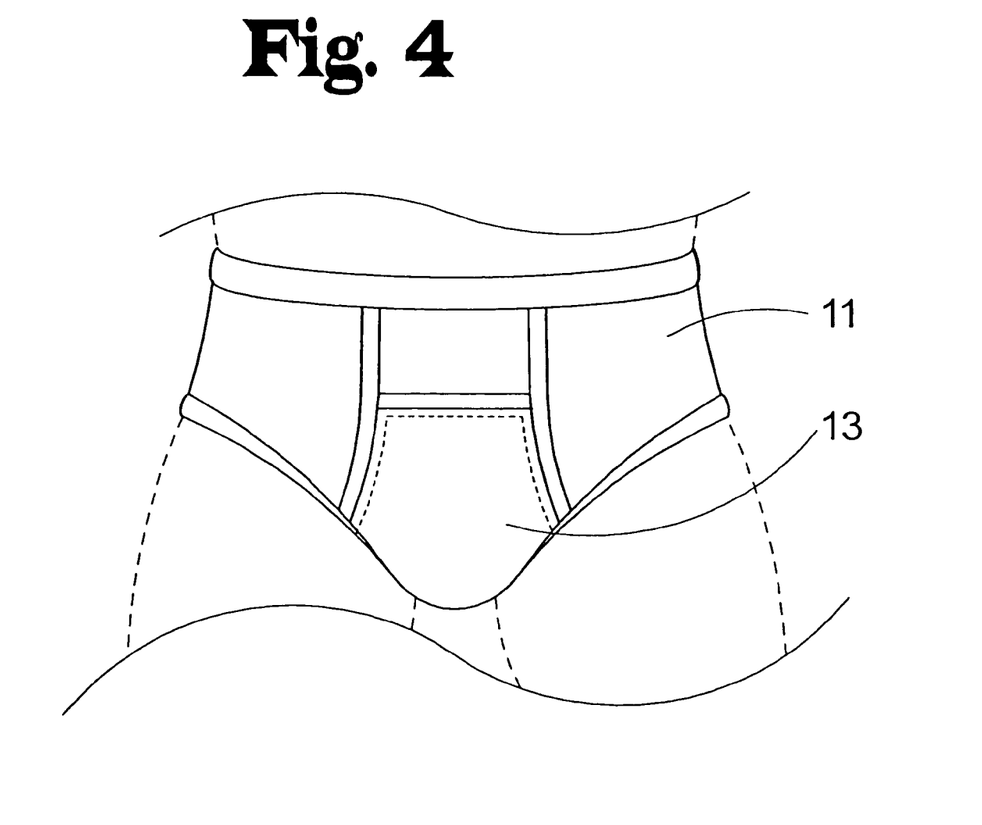
FIG. 4 is a front view of the present invention for a male user.
Figure 5:
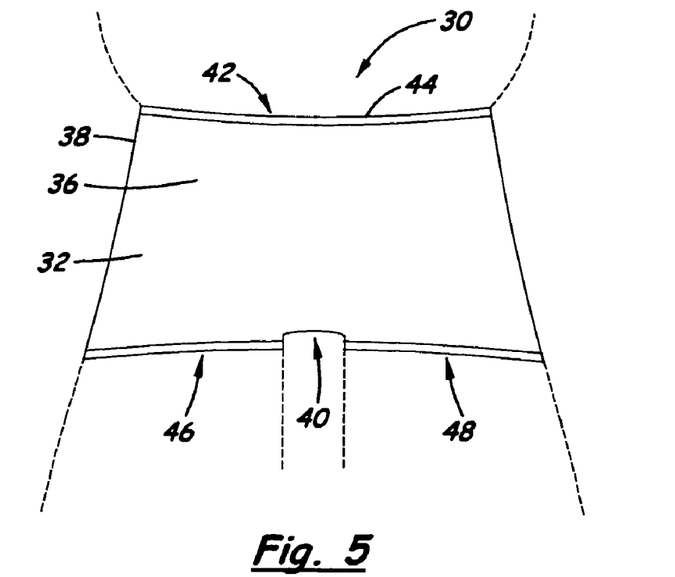
FIG. 5 is a front view of a second embodiment of the present invention particularly showing an outer part of the undergarment system.
Figure 6:
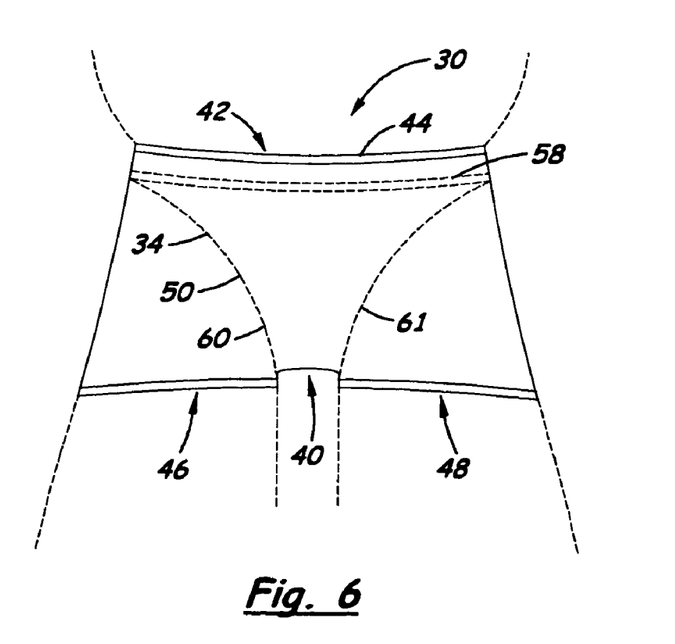
FIG. 6 is a front view of the second embodiment of the present invention particularly showing an inner part with the outer part shown in broken lines.
Figure 7:
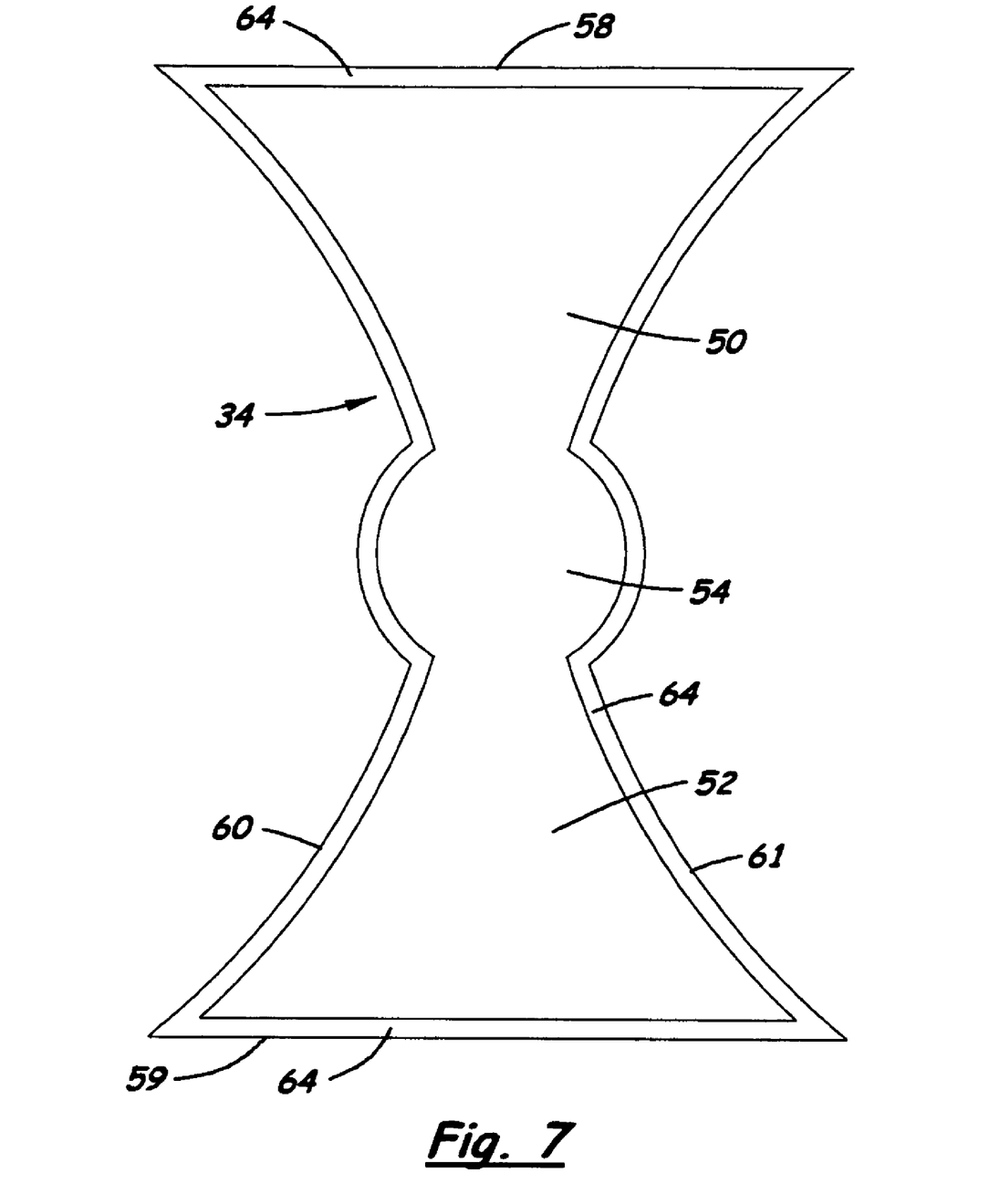
FIG. 7 is a top view of the inner part of the second embodiment particularly.

In another embodiment of the invention, shown in FIGS. 5 through 7, a protective undergarment system 30 for absorbing fluids released by a body of a user to protect the garments being worn by the user is disclosed. The protective undergarment system 30 may comprise an outer member 32 and an inner member 34. The outer member 32 is positionable around the abdomen, groin and posterior of the user. The outer member 32 has a front portion 36, a rear portion 38, and a crotch portion 40 extending between the front portion 36 and the rear portion 38. The outer member 32 may have an upper aperture 42 for positioning about the abdomen of the user. The outer member 32 also has a waist edge 44 located along a perimeter of the upper aperture 42. The outer member 32 has a pair of leg apertures 46, 48 that are positioned under the upper aperture 42 for each receiving one of the legs of the user.

The inner member 34 is configured to absorb fluids released by the body, and may be removed from the outer member 32 when the inner member is soiled. The inner member 34 is removably coupled to the outer member 32 such that the inner member is selectively positionable inside of the outer member and between an inner surface of the outer member and the abdomen of the user when the outer member is worn. The inner member 34 is positioned between the pair of leg apertures 46, 48.

The inner member 34 my have a front portion 50 and a rear portion 52 located at opposite ends of the inner member. The front portion 50 may have a substantially triangular shape, and the rear portion 52 may have a substantially triangular shape. The inner member 34 may have a central portion 54 that is positioned between the front portion 50 and the rear portion 52 of the inner member. The central portion 54 may be positioned between the pair of leg apertures 46, 48 when the inner member 34 is located inside of the outer member 32. The central portion 54 may be substantially circular in shape.

The inner member 34 may have a perimeter edge 56. The perimeter edge 56 may include opposite end edges 58, 59. The opposite end edges 58, 59 may be positioned substantially adjacent to opposite portions of the waist edge 44 when the inner member 34 is positioned inside of the outer member. In some embodiments, the opposite end edges 58, 59 are substantially linear or straight. The perimeter edge 56 of the inner member 34 may also include opposite side edges 60, 61. Sections of the side edges 60, 61 located along the front portion 50 may converge toward the central portion 54. Similarly, sections of the side edges 60, 61 located along the rear portion 52 may converge toward the central portion 54. In some embodiments, the end edges 58, 59 and the side edges 60, 61 along the front portion 50 and the rear portion 52 may form a generally hourglass shape to facilitate the fit against the body of the wearer.

In various embodiments, the outer member is continuous and unbroken along and about the upper aperture 42 of the outer member, and the outer member is also continuous and unbroken along and about each leg aperture of the pair of leg apertures 46, 48.

A fastener element 64 may be united to the inner member 34 and may be configured to secure the inner member 34 to the outer member 32. The fastener element 64 may be positioned along at least a portion of a perimeter edge 56 and may be positioned adjacent to the perimeter edge of the inner member 34. The fastener element 64 may extend along substantially an entirety of the perimeter of the inner member. In some embodiments of the invention, the fastener element comprises an adhesive that is applied to the inner member at the described locations. The adhesive may be applied to a secondary element, and the secondary element may be applied to the inner member.

The outer member may be fabricated from a knitted elastic nylon, and may be of any style, such as boxer style.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A protective undergarment system for absorbing fluids released by a body of a user to protect the garments being worn by the user, the protective undergarment system comprising:
   an outer member for being selectively positioned around an abdomen, a groin and a posterior of the user, the outer member having a front portion and a rear portion and a crotch portion extending between the front portion and the rear portion, the outer member having an upper aperture for positioning about the abdomen of the user, the outer member having a waist edge located along a perimeter of the upper aperture, the outer member having a pair of leg apertures positioned under the upper aperture for each receiving one of the legs of the user; and
   an inner member for absorbing the fluids released by the body such that the inner member can be removed from the outer member when the inner member is soiled, the inner member being removably coupled to the outer member such that the inner member is selectively positioned inside of the outer member and between an inner surface of the outer member and the abdomen of the user when the outer member is worn, the inner member being positioned between the pair of leg apertures; and
   a fastener element being united to the inner member and being configured to secure the inner member to the outer member;
   wherein the inner member has a front portion, a rear portion located at opposite ends of the inner member, and a central portion positioned between the front portion and the rear portion of the inner member.

2. The system of claim 1 wherein the front portion has a substantially triangular shape and the rear portion has a substantially triangular shape.

3. The system of claim 1 wherein the central portion is positioned between the pair of leg apertures when the inner member is located inside of the outer member, and the central portion is substantially circular.

4. The system of claim 1 wherein the inner member a perimeter edge, the perimeter edge including opposite end edges, the opposite end edges being positioned substantially adjacent to opposite portions of the waist edge when the inner member is positioned inside of the outer member, the opposite end edges being substantially linear.

5. The system of claim 4 wherein the perimeter edge of the inner member includes opposite side edges, sections of the side edges along the front portion converging toward the central portion, sections of the side edges along the rear portion converging toward the central portion.

6. The system of claim 5 wherein the side edges and the end edges along the front portion and the rear portion form a generally hourglass shape.

7. The system of claim 1 wherein the outer member is continuous and unbroken along and about the upper aperture of the outer member; and
   wherein the outer member is continuous and unbroken along and about each the leg aperture of the pair of leg apertures.

8. The system of claim 1 wherein the fastener element is positioned along at least a portion of a perimeter edge of the inner member.

9. The system of claim 8 wherein the fastener element is positioned adjacent to a perimeter edge of the inner member.

10. The system of claim 9 wherein the fastener element extends along substantially an entirety of the perimeter of the inner member.

11. The system of claim 1 wherein the front portion has a substantially triangular shape and the rear portion has a substantially triangular shape;
   wherein the central portion is positioned between the pair of leg apertures when the inner member is located inside of the outer member, and the central portion is substantially circular;
   wherein the inner member a perimeter edge, the perimeter edge including opposite end edges, the opposite end edges being positioned substantially adjacent to opposite portions of the waist edge when the inner member is positioned inside of the outer member, the opposite end edges being substantially linear;
   wherein the perimeter edge of the inner member includes opposite side edges, sections of the side edges along the front portion converging toward the central portion, sections of the side edges along the rear portion converging toward the central portion;
   wherein the side edges and the end edges along the front portion and the rear portion form a generally hourglass shape;
   wherein the outer member is continuous and unbroken along and about the upper aperture of the outer member;
   wherein the outer member is continuous and unbroken along and about each the leg aperture of the pair of leg apertures;
   wherein the fastener element is positioned along at least a portion of a perimeter edge of the inner member;
   wherein the fastener element is positioned adjacent to a perimeter edge of the inner member; and
   wherein the fastener element extends along substantially an entirety of the perimeter of the inner member.

12. A protective undergarment system for absorbing fluids released by a body of a user to protect the garments being worn by the user, the protective undergarment system comprising:
   an upper member for being selectively positioned around an abdomen, a groin and a posterior of the user, the upper member having a front portion and a rear portion and a crotch portion extending between the front portion and the rear portion, the upper member having an upper aperture for positioning about the abdomen of the user, the upper member having a pair of leg apertures positioned under the upper aperture for each receiving one of the legs of the user, the upper member further having a lower aperture extending through the upper member between the leg apertures such that the lower aperture is positioned between the legs of the user when the upper member is being worn by the user, the lower aperture extending through the crotch portion of the upper member and into the front portion and into the rear portion; and
   a lower member being removably coupled to the upper member such that the lower member is selectively positioned over the lower aperture of the upper member to selectively close the lower aperture of the upper member, the lower member being adapted for absorbing the fluids released by the body such that the lower member can be removed from the lower member when the lower member is soiled;

wherein the upper member is continuous and unbroken along and about the upper aperture of the upper member;

wherein the upper member is continuous and unbroken along and about each the leg aperture of the pair of leg apertures;

a first fastener member united to the lower member and being positioned along and adjacent to a perimeter edge of the lower member; and a second fastener member united to the upper member and being positioned along and adjacent to a perimeter edge defining the lower aperture of the upper member;

wherein the first fastener member is complimentary to the second fastener member such that the first fastener member is removably fastened to the second fastener member to secure the lower member to the upper member.

13. The protective undergarment system of claim 12 wherein the upper member has an edge defining the upper aperture, the edge defining the upper aperture of the upper member being continuous and unbroken along and about the upper aperture; and wherein the upper member has an edge defining each of the leg apertures, and the edges defining the respective leg apertures are each continuous and unbroken along and about each the leg aperture of the pair of leg apertures.

14. The protective undergarment system of claim 12 wherein the first fastener member comprises a first portion of hook and loop fastener, the second fastener member comprises a second portion of hook and loop fastener, the first portion of hook and loop fastener being complimentary to the second portion of hook and loop fastener such that the first portion of hook and loop fastener is selectively coupled to the second portion of hook and loop fastener to selectively couple the lower member to the upper member.

15. The protective undergarment system of claim 12 wherein the lower member being elongate with a pair of end portions and a medial portion between the end portions, the lower member tapering narrower in width from the end portions toward the medial portion such that the lower member is generally hourglass shaped to inhibit the lower member from bunching up between the legs of the user when the upper member and lower member are worn.

16. The protective undergarment system of claim 12 wherein the lower aperture extends a distance into the front portion of the upper member that is substantially equal to a distance that the lower aperture extends into the front portion of the upper member.

17. The protective undergarment system of claim 12 wherein the lower aperture extends a distance into the front portion of the upper member that is approximately one half of a distance between the crotch portion and the upper opening, the lower aperture extending a distance into the rear portion of the upper member that is approximately one half of a distance between the crotch portion and the upper opening.

18. The protective undergarment system of claim 12 wherein the upper member comprises a flexible material for conforming to the abdomen, groin and posterior of the user to provide a comfortable fit for the user; and wherein the lower member comprises an absorbent material, the absorbent material being adapted for absorbing the fluids released by the body of the user, the absorbent material being adapted for being discarded to allow the user to reuse the upper member when the lower member becomes soiled.

19. The protective undergarment system of claim 12 wherein the upper member has an edge defining the upper aperture, the edge defining the upper aperture of the upper member being continuous and unbroken along and about the upper aperture;

wherein the upper member has an edge defining each of the leg apertures, and the edges defining the respective leg apertures are each continuous and unbroken along and about each the leg aperture of the pair of leg apertures;

wherein the first fastener member comprises a first portion of hook and loop fastener, the second fastener member comprises a second portion of hook and loop fastener, the first portion of hook and loop fastener being complimentary to the second portion of hook and loop fastener such that the first portion of hook and loop fastener is selectively coupled to the second portion of hook and loop fastener to selectively couple the lower member to the upper member;

wherein the lower member being elongate with a pair of end portions and a medial portion between the end portions, the lower member tapering narrower in width from the end portions toward the medial portion such that the lower member is generally hourglass shaped to inhibit the lower member from bunching up between the legs of the user when the upper member and lower member are worn;

wherein the lower aperture extends a distance into the front portion of the upper member that is substantially equal to a distance that the lower aperture extends into the front portion of the upper member;

wherein the lower aperture extends a distance into the front portion of the upper member that is approximately one half of a distance between the crotch portion and the upper opening, the lower aperture extending a distance into the rear portion of the upper member that is approximately one half of a distance between the crotch portion and the upper opening;

wherein the upper member comprises a flexible material for conforming to the abdomen, groin and posterior of the user to provide a comfortable fit for the user; and wherein the lower member comprises an absorbent material, the absorbent material being adapted for absorbing the fluids released by the body of the user, the absorbent material being adapted for being discarded to allow the user to reuse the upper member when the lower member becomes soiled.

20. A protective undergarment system for absorbing fluids released by a body of a user to protect the garments being worn by the user, the protective undergarment system comprising:

an outer member for being selectively positioned around an abdomen, a groin and a posterior of the user, the outer member having a front portion and a rear portion and a crotch portion extending between the front portion and the rear portion, the outer member having an upper aperture for positioning about the abdomen of the user, the outer member having a waist edge located along a perimeter of the upper aperture, the outer member having a pair of leg apertures positioned under the upper aperture for each receiving one of the legs of the user;

an inner member for absorbing the fluids released by the body such that the inner member can be removed from the outer member when the inner member is soiled, the inner member being removably coupled to the outer member such that the inner member is selectively positioned inside of the outer member and between an inner surface of the outer member and the abdomen of the user when the outer member is worn, the inner member being positioned between the pair of leg apertures;

a first fastener member united to the lower member and being positioned along and adjacent to a perimeter edge of the lower member; and a second fastener member united to the upper member and being positioned along and adjacent to a perimeter edge defining the lower aperture of the upper member;

wherein the first fastener member is complimentary to the second fastener member such that the first fastener member is removably fastened to the second fastener member to secure the lower member to the upper member.

* * * * *